(12) United States Patent
Chen-Sarkanen et al.

(10) Patent No.: US 9,796,993 B2
(45) Date of Patent: Oct. 24, 2017

(54) LIGNIN-DEGRADING METHODS

(71) Applicant: REGENTS OF THE UNIVERSITY OF MINNESOTA, Minneapolis, MN (US)

(72) Inventors: Yi-ru Chen-Sarkanen, New Brighton, MN (US); Simo Sarkanen, New Brighton, MN (US); Yun-Yan Wang, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 126 days.

(21) Appl. No.: 14/364,448

(22) PCT Filed: Dec. 12, 2012

(86) PCT No.: PCT/US2012/069243
§ 371 (c)(1),
(2) Date: Jun. 11, 2014

(87) PCT Pub. No.: WO2013/090430
PCT Pub. Date: Jun. 20, 2013

(65) Prior Publication Data
US 2014/0335571 A1 Nov. 13, 2014

Related U.S. Application Data

(60) Provisional application No. 61/569,474, filed on Dec. 12, 2011, provisional application No. 61/709,594, filed on Oct. 4, 2012.

(51) Int. Cl.
C12P 19/14 (2006.01)
C12P 19/02 (2006.01)
C12P 19/00 (2006.01)

(52) U.S. Cl.
CPC .............. *C12P 19/02* (2013.01); *C12P 19/00* (2013.01); *C12P 19/14* (2013.01)

(58) Field of Classification Search
None
See application file for complete search history.

(56) References Cited

FOREIGN PATENT DOCUMENTS

WO  00/73426 A1  12/2000
WO  2013/090430 A1  6/2013

OTHER PUBLICATIONS

Vanholme et al., Plant Physiology, 2010, vol. 153, p. 895-905.*
Perez et al., Int. Microbiol., 2002, vol. 5, p. 53-63.*
Jönsson et al., Appl Microbiol Biotechnol, 1998, vol. 49, p. 691-697.*
Mswaka et al., Mycol. Res. 1998, vol. 102, No. 11, p. 1399-1404.*
Kirk et al., "Use of Fungi in Pulping Wood: An Overview of Biopulping Research", Chapter 7. of Frontiers in Industrial Mycology, edited by Gary F. Leatham, 1992, Routledge, Chapman & Hall Inc.*
Nakamura et al., Biodegradation, published online Nov. 2011, vol. 23, p. 343-350.*
Berrin et al., "Exploring the Natural Fungal Biodiversity of Tropical and Temperate Forests toward Improvement of Biomass Conversion," *Applied and Environmental Microbiology*, Sep. 2012; 78(18):6483-6490.
Bourbonnais et al., "Electrochemical analysis of the interactions of laccase mediators with lignin model compounds," *Biochem. Biophys. Acta.*, Mar. 2, 1998; 1379(3):381-390.
Chen et al., "Macromolecular replication during lignin biosynthesis," *Phytochemistry*, Mar. 2010; 71(4):453-462.
Chen et al., "Enzyme-catalyzed degradation of native polymeric lignin in homogeneous solution," *BioEnergy Science Center*, Retreat poster presentation, Jun. 2010.
Chen et al., "Biodegradation of Native Lignin Domains," *BioEnergy Science Center*, Retreat poster and presentation, Jul. 2011.
Chen et al., "Common themes in Lignin Biosynthesis and Lignin Biodegradation," Abstract presented at the *Phytochemical Society of North America, 50th Anniversary Meeting*, Dec. 15, 2011, Hawaii, USA.
Chen et al., "Lignin-Degrading Enzyme Activities," in *Methods in Molecular Biology: Biomass Conversion*, 2012; M.E. Himmel (Ed.), Humana Press, New York, Chapter 21:251-268.
Contreras et al., "Propensity of Lignin to Associate: Light Scattering Photometry Study with Native Lignins," *Biomacromolecules*, 2008; 9(12):3362-3369. Available online Nov. 8, 2008.
Guan et al., "Dehydrogenative polymerization of coniferyl alcohol on macromolecular lignin templates," *Phytochemistry*, Jul. 1997; 45(5):911-918.
Hammel et al., "Ligninolysis by a Purified Lignin Peroxidase," *J. Biol. Chem.*, Jun. 15, 1993; 268(17):12274-12281.
Hammel et al., "Role of fungal peroxidases in biological ligninolysis," *Current Opinion in Plant Biology*, 2008; 11:349-355.
International Search Report and Written Opinion, dated Mar. 12, 2013, for International Application No. PCT/US2012/069243, filed Dec. 12, 2012; 12 pages.
International Preliminary Report on Patentability, dated Jun. 17, 2014, for International Application No. PCT/US2012/069243, filed Dec. 12, 2012; 8 pages.
Langston et al., "Oxidoreductive Cellulose Depolymerization by the Enzymes Cellobiose Dehydrogenase and Glycoside Hydrolase 61," *Applied and Environmental Microbiology*, Oct. 2011; 77(19):7007-7015.
Lundquist et al., "Isolation of lignin by means of liquid-liquid extraction," *Svensk Papperstidn*, 1977; 80(5):143-144.
MacDonald et al., "Transcriptomic Responses of the Softwood-Degrading White-Rot Fungus *Phanerochaete carnosa* during Growth on Coniferous and Deciduous Wood," *Applied and Environmental Microbiology*, May 2011; 77(10):3211-3218.

(Continued)

Primary Examiner — Kade Ariani
(74) Attorney, Agent, or Firm — Mueting, Raasch & Gebhardt, PA

(57) ABSTRACT

A method involving degrading materials that include lignin generally includes contacting a lignin sample with a flavin-dependent monooxygenase and contacting the lignin sample with an auxiliary compound.

8 Claims, 12 Drawing Sheets

(56) References Cited

OTHER PUBLICATIONS

Nakamura et al., "Flavin-containing monooxygenases from *Phanerochaete chrysosporium* responsible for fungal metabolism of phenolic compounds," *Biodegradation*, 2012; 23:343-350.

Quinlan et al., "Insights into the oxidative degradation of cellulose by a copper metalloenzyme that exploits biomass components," *PNAS USA*, Sep. 13, 2011; 108(37):15079-15084.

Reynolds et al., "Transmembrane Topology and Signal Peptide Prediction Using Dynamic Bayesian Networks," *PLoS Computational Biology*, Nov. 7, 2008; 4(11):e1000213.

Sarkanen, "Lignin Biosynthesis, Biodegradation and Derivative Plastics," University of Minnesota CRIS, project start date: Oct. 1, 2010; pp. 1-18.

Sluiter et al., "Determination of Structural Carbohydrates and Lignin in Biomass," *National Renewable Energy Laboratory*, Technical Report NREL/TP-510-42618; Revised Jul. 2011: 1-15.

Suzuki et al., "Hydroxylation of o-Halogenophenol and o-Nitrophenol by Salicylate Hydroxylase," *J. Biochem.*, Feb. 1991; 109(2):348-353.

Wariishi et al, "In vitro depolymerization of lignin by manganese peroxidase of Phanerochaete chrysosporium," *Biochem. Biophys. Res. Commun.*, Apr. 15, 1991; 176(1):269-275.

Wei et al., "Laccase and Its Role in Production of Extracellular Reactive Oxygen Species during Wood Decay by the Brown Rot Basidiomycete *Postia placenta*," *Applied and Environmental Microbiology*, Apr. 2010; 76(7):2091-2097.

Wyatt, "Light scattering and the absolute characterization of macromolecules," *Anal. Chim. Acta*, Feb. 1, 1993; 272(1):1-40.

Yelle et al., "Multidimensional NMR analysis reveals truncated lignin structures in wood decayed by the brown rot basidiomycete *Postia placenta,*" *Environmental Microbiology*, 2011; 13(4):1091-1100.

Zifcakova et al., "Fungal polysaccharide monooxygenases: new players in the decomposition of cellulose," *Fungal Ecology*, Jul. 7, 2012; 481-489.

\* cited by examiner

US 9,796,993 B2

LIGNIN-DEGRADING METHODS

CROSS-REFERENCE TO RELATED APPLICATION

This application is the §371 U.S. National Stage of International Application No. PCT/US2012/069243, filed 12 Dec. 2012, which claims the benefit of U.S. Provisional Patent Application Ser. No. 61/709,594, filed Oct. 4, 2012, and claims the benefit of U.S. Provisional Patent Application Ser. No. 61/569,474, filed Dec. 12, 2011, each of which is incorporated herein by reference in its entirety.

GOVERNMENT FUNDING

This invention was made with government support under XFT-8-88522-01 awarded by the Department of Energy. The government has certain rights in the invention.

SUMMARY OF THE INVENTION

In one aspect, the invention provides a method that generally includes contacting a lignin sample with a lignin depolymerase, and contacting the lignin sample and/or lignin depolymerase with an auxiliary compound. In some cases, the lignin sample can include native lignin.

In some embodiments, the lignin depolymerase can include an enzyme expressed in the secretome of a fungus such as, for example, a white-rot fungus or a brown-rot fungus.

In some embodiments, the lignin depolymerase can include a flavin-dependent monooxygenase such as, for example, salicylate hydroxylase or a homologous flavin-dependent monooxygenases. In other embodiments, the lignin depolymerase can include a peroxidase, β-etherase, or a laccase.

In some embodiments, the method can further include sequestering lignin components produced from lignin macromolecules in the lignin sample by contacting the lignin sample with the lignin depolymerase.

In another aspect, the invention provides a method that generally includes contacting an auxiliary compound with a sample that includes (a) uncleaved lignin macromolecules and/or (b) at least partially cleaved lignin components in intermolecular association with one another or with at least a portion of the uncleaved lignin macromolecules. In the method of this aspect, the auxiliary compound dissociates the at least partially cleaved lignin components from one another and/or from the uncleaved lignin macromolecules.

In the method of either aspect, the auxiliary compound can include a protein expressed in the secretome of a fungus. In some embodiments, the auxiliary compound may be an analog of a natural auxiliary compound.

In some embodiments, the auxiliary compound such as, for example, a cellulase, a hemicellulase, a protease, or a glycoside hydrolase, may adsorb to a lignin domain or to a lignin depolymerase molecule.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
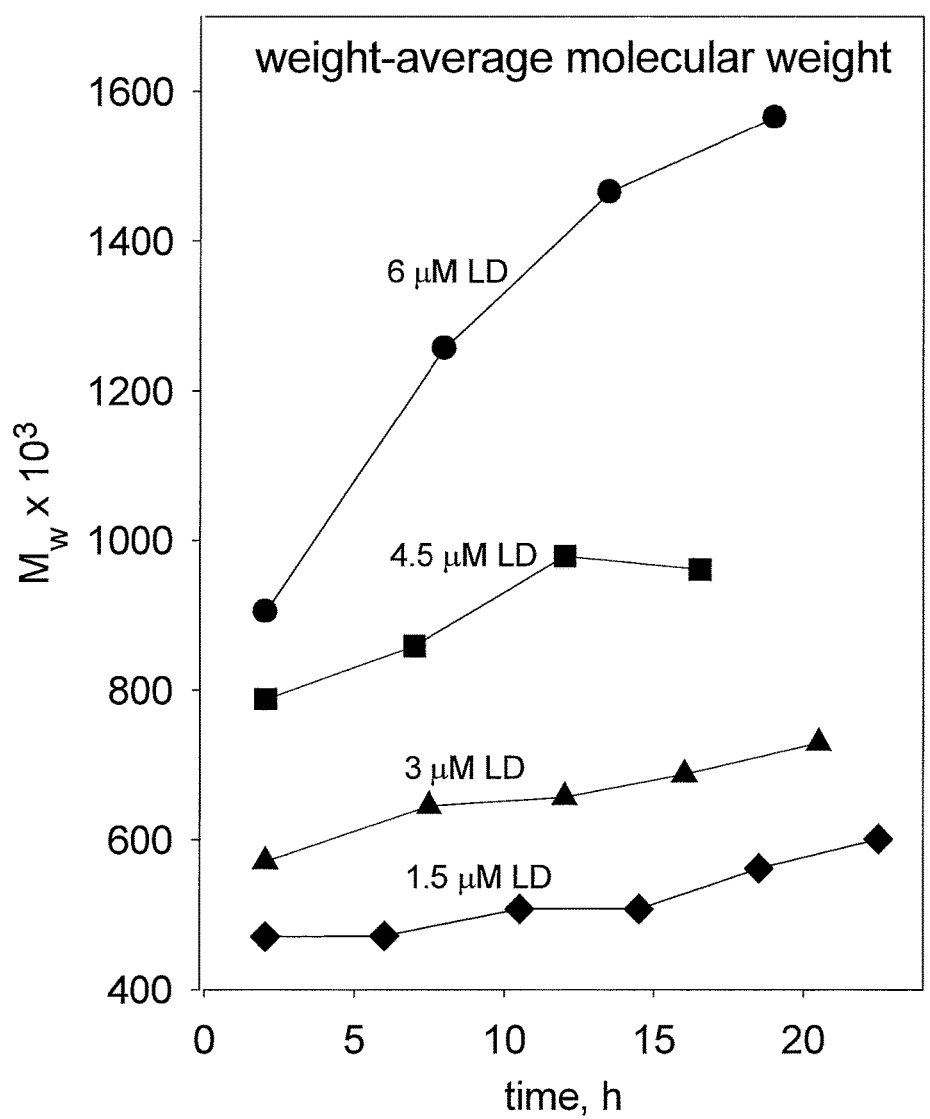
FIG. 1. Changes in weight-average molecular weight of soluble native polymeric lignin preparation caused by lignin depolymerase at pH 6.3 in 25 mM phosphate containing 30 µM NADH.

We have recognized that enzyme-catalyzed degradation of lignin domains—including those of native lignin—can involve two steps. The first step involves cleaving the lignin macromolecules. The second step involves dissociating the degraded components from the other lignin polymer chains and/or the lignin depolymerizing enzyme. The noncovalent forces between the substructures in interacting lignin macromolecules arise primarily from electron correlation, and they are remarkably strong. Thus, one enzyme can bring about lignin depolymerization, and an auxiliary compound may be responsible for causing dissociation of the cleaved components.

The depolymerization and dissociation of lignin has potential applications in any kind of biochemical and/or biological degradation of lignocellulosic materials, including native lignin, in which the constituent biopolymers have not been extensively derivatized or modified with respect to their native configuration. For example, the conversion of lignocellulose to liquid biofuels can involve three main steps: pretreatment, saccharification, and fermentation. The pretreatment step is typically the most expensive unit-operational process. Conventional pretreatment conditions (e.g., dilute aqueous acid at elevated temperature) tend to reduce the impact of the lignin as a barrier toward the subsequent action of cellulases and hemicellulases during saccharification of their polysaccharide substrates. Practicing the methods described herein in place of or in addition to conventional pretreatment steps can reduce the cost of the most expensive of the three steps, and should have a substantial impact upon the economic viability of producing liquid fuels or other commodity organic chemicals from lignocellulose.

Moreover, the method described herein has general utility among various applications that involve converting biomass to commercially relevant products. For example, one may combine pretreatment with saccharification during the standard "simultaneous saccharification and fermentation" (SSF) approach to converting plant biomass to ethanol or isobutanol (the latter being a convenient intermediate in the production of drop-in jet fuels). Similar considerations apply to the production of any other organic chemical from lignocellulose through a process involving pretreatment, saccharification, and fermentation. Alternatively, in the context of traditionally pulping—i.e., by chemical means—lignocellulose to cellulosic fibers for making paper, the use of effective lignin-degrading enzymes can reduce the cost of bleaching the pulp before feeding the material to a paper machine. Moreover, lignin-degrading enzymes may help to reduce the overall costs and use of chemicals in biochemical/biological pulping ("biopulping").

There is no existing enzymatic basis for degrading native lignin preparations from, or domains in, lignocellulosic plant materials. The best that can be achieved with the enzymes studied so far—namely, lignin peroxidase, manganese peroxidase, and the laccase-mediator system—is a balance between lignin degradation and either polymerization or repolymerization. Broadly speaking, the substructures in lignin macromolecules may be either phenolic or nonphenolic. The phenolic residues are easier to (one-electron) oxidize, and the resulting phenoxy radicals readily undergo polymerization leading to an increase in the molecular weight of the lignin components that are affected. On the other hand, if the enzyme is capable of (one-electron) oxidation of a nonphenolic lignin substructure, the subsequent transformations of the resulting cation radical often lead to the formation of a phenoxy radical which again will readily undergo polymerization.

The methods described herein employ an entirely different approach to depolymerizing lignins. The cleavage of lignin macromolecules is brought about by an enzyme acting as a lignin depolymerase, described in more detail below, whereupon the degraded lignin components may undergo association more extensively, leading to an increase in substrate molecular weight as the radius of gyration falls markedly. Thereafter, dissociation of the associated lignin complexes may be engendered by an auxiliary compound, also described in more detail below. Interestingly, in cases where the auxiliary compound may be an enzyme, the dissociative activity of the auxiliary compound appears to be independent of its traditional catalytic capacity as an enzyme.

In direct contrast to the attempted degradation of lignin using previously studied enzymes, like peroxidases or laccases, the methods described herein may be performed using proteins that are incapable of polymerizing macromolecular lignin components.

In nature, the biological agents of lignin biodegradation are primarily white-rot basidiomycetous fungi. Brown-rot fungi, which are genetically closely related to white-rot fungi, also modify lignins but without extensively degrading them. Flavin-dependent monooxygenases such as, for example, salicylate hydroxylase and homologs thereof are prominently present in the secretomes of many white-rot fungi such as, for example, *Phanerochaete chrysosporium*, *Trametes versicolor*, and *Heterobasidion annosum*, and also in that of the brown-rot fungus, *Postia placenta*.

Flavin-dependent monooxygenases represent exemplary lignin depolymerase enzymes in the methods described herein. Exemplary lignin depolymerases include those that hydroxylate aromatic rings. These enzymes may exhibit considerable substrate versatility (J. Biochem. 109 (1991) 348-353). Thus, exemplary lignin depolymerases can include, for example, salicylate monooxygenase (EC 1.14.13.1), 4-hydroxybenzoate monooxygenase (EC 1.14.13.2 and EC 1.14.13.33), 4-hydroxyphenylacetate monooxygenase (EC 1.14.13.3), melilotate monooxygenase (EC 1.14.13.4), imidazoleacetate monooxygenase (EC 1.14.13.5), orcinol monooxygenase (EC 1.14.13.6), phenol monooxygenase (EC 1.14.13.7), kynurenine monooxygenase (EC 1.14.13.9), 2,6-dihydroxypyridine monooxygenase (EC 1.14.13.10), 4-hydroxyphenylacetate monooxygenase (EC 1.14.13.18), taxifolin monooxygenase (EC 1.14.13.19), 2,4-dichlorophenol monooxygenase (EC 1.14.13.20), 3-hydroxybenzoate monooxygenase (EC 1.14.13.23 and EC 1.14.13.24), 4-aminobenzoate monooxygenase (EC 1.14.13.27), anthranilate monooxygenase (EC 1.14.13.35), anhydrotetracycline monooxygenase (EC 1.14.13.38), anthraniloyl-CoA monooxygenase (EC 1.14.13.40), 2-hydroxybiphenyl monooxygenase (EC 1.14.13.44), pentachlorophenol monooxygenase (EC 1.14.13.50), benzoyl-CoA monooxygenase (EC 1.14.13.58), 3-hydroxyphenylacetate monooxygenase (EC 1.14.13.63), 4-hydroxybenzoate monooxygenase (EC 1.14.13.64), 4-methyl-5-nitrocatechol monooxygenase, 4-aminobenzoate monooxygenase, and 2-octaprenyl-6-methoxyphenol monooxygenase. Additional exemplary flavoproteins that may serve as a lignin depolymerase are listed in Table I.

TABLE I

Flavoproteins in Secretomes of White-rot and Brown-rot Fungi

| | | | SignalP 3.0[d] | | | |
|---|---|---|---|---|---|---|
| Protein ID[a] | E-Value[b] | JGI[c] | NN | HMM | Phobius[e] | Philius[e] |
| *Pleurotus ostreatus* (white-rot) | | | | | | |
| 1050021 | 1.45E−57 | ✓ | | ✓ | | |
| 1104438 | 2.02E−52 | | | | ✓ | ✓ |

TABLE I-continued

Flavoproteins in Secretomes of White-rot and Brown-rot Fungi

| Protein ID[a] | E-Value[b] | JGI[c] | SignalP 3.0[d] NN | HMM | Phobius[e] | Philius[e] |
|---|---|---|---|---|---|---|
| 1077335 | 7.83E−50 | ✓ | | ✓ | ✓ | ✓ |
| 1102164 | 4.48E−42 | ✓ | | | | ✓ |
| 1020351 | 1.23E−38 | ✓ | | ✓ | | |
| 1043408 | 5.18E−31 | | | | ✓ | ✓ |
| 1076617 | 1.63E−26 | ✓ | | | | |
| 1097984 | 4.78E−16 | ✓ | ✓ | ✓ | | ✓ |
| 176495 | 3.03E−11 | | | | | |
| 1020141 | 3.26E−06 | | | | | |
| 1059476 | 7.65E−06 | | | | | |
| Total no.: | | 6 | 1 | 4 | 3 | 5 |

*Phanerochaete chrysosporium* (white-rot)

| Protein ID | E-Value | JGI | NN | HMM | Phobius | Philius |
|---|---|---|---|---|---|---|
| 123956 | 2.53E−50 | | | | | |
| 912 | 4.87E−38 | | | | | |
| 8207 | 3.56E−34 | ✓ | | ✓ | | |
| 9392 | 1.96E−30 | ✓ | ✓ | | ✓ | ✓ |
| 8209 | 6.90E−26 | | | | | ✓ |
| 8210 | 1.87E−23 | ✓ | | ✓ | ✓ | ✓ |
| 8203 | 6.30E−23 | ✓ | | ✓ | ✓ | ✓ |
| 8208 | 6.95E−19 | ✓ | | ✓ | ✓ | ✓ |
| 39337 | 5.71E−13 | ✓ | ✓ | ✓ | | ✓ |
| 8714 | 1.90E−12 | ✓ | | ✓ | ✓ | ✓ |
| 140880 | 3.07E−11 | | | | | |
| 7965 | 7.45E−11 | ✓ | ✓ | ✓ | ✓ | ✓ |
| 130811 | 1.96E−10 | ✓ | ✓ | ✓ | ✓ | ✓ |
| 2225 | 2.43E−10 | ✓ | ✓ | ✓ | ✓ | ✓ |
| 140680 | 1.33E−09 | ✓ | ✓ | ✓ | ✓ | ✓ |
| 7979 | 2.52E−09 | ✓ | ✓ | ✓ | ✓ | ✓ |
| 130719 | 4.40E−09 | ✓ | ✓ | ✓ | ✓ | ✓ |
| 140831 | 8.16E−09 | ✓ | | ✓ | ✓ | ✓ |
| 29638 | 4.50E−08 | ✓ | ✓ | ✓ | | |
| 898 | 5.88E−08 | ✓ | | ✓ | ✓ | ✓ |
| 7961 | 1.57E−06 | | ✓ | | | ✓ |
| 2195 | 6.38E−06 | | | | | |
| 7978 | 7.57E−06 | ✓ | ✓ | ✓ | ✓ | ✓ |
| Total no.: | | 17 | 12 | 16 | 13 | 16 |

*Ceriporiopsis subvermispora* (white-rot)

| Protein ID | E-Value | JGI | NN | HMM | Phobius | Philius |
|---|---|---|---|---|---|---|
| 90429 | 4.34E−68 | ✓ | | ✓ | ✓ | ✓ |
| 50626 | 1.47E−67 | | | ✓ | | |
| 104377 | 1.22E−55 | ✓ | | ✓ | ✓ | ✓ |
| 123655 | 2.71E−53 | ✓ | ✓ | ✓ | ✓ | ✓ |
| 106536 | 2.64E−49 | | | | ✓ | ✓ |
| 137302 | 3.54E−45 | | | | | |
| 114455 | 1.16E−44 | ✓ | ✓ | ✓ | ✓ | ✓ |
| 151487 | 1.16E−43 | | | | | |
| 115693 | 1.82E−36 | ✓ | ✓ | | | |
| 95996 | 4.14E−36 | ✓ | ✓ | ✓ | | ✓ |
| 74585 | 2.03E−30 | | | | | |
| 119636 | 4.98E−22 | ✓ | ✓ | ✓ | ✓ | ✓ |
| 120062 | 6.09E−21 | | | ✓ | | |
| 155529 | 5.36E−12 | ✓ | ✓ | ✓ | | ✓ |
| 103994 | 8.09E−08 | ✓ | | ✓ | ✓ | ✓ |
| 104141 | 6.40E−06 | | | | | |
| Total no.: | | 9 | 6 | 10 | 8 | 8 |

*Trametes versicolor* (white-rot)

| Protein ID | E-Value | JGI | NN | HMM | Phobius | Philius |
|---|---|---|---|---|---|---|
| 43869 | 8.08E−71 | | | | ✓ | ✓ |
| 41389 | 5.92E−65 | ✓ | | ✓ | | ✓ |
| 162167 | 1.42E−60 | | | | | |
| 58559 | 2.02E−59 | ✓ | | ✓ | ✓ | ✓ |
| 32834 | 2.32E−56 | | | | | |
| 53220 | 3.73E−49 | ✓ | ✓ | | | ✓ |
| 116325 | 1.67E−41 | ✓ | | ✓ | | |
| 45010 | 3.95E−35 | ✓ | ✓ | ✓ | ✓ | ✓ |
| 37799 | 2.21E−31 | | | | | |
| 175239 | 1.21E−21 | | | | | |
| 51597 | 2.85E−16 | ✓ | | | | ✓ |
| 42884 | 1.34E−10 | ✓ | ✓ | ✓ | ✓ | ✓ |
| 114069 | 6.65E−10 | ✓ | ✓ | ✓ | ✓ | ✓ |
| 57395 | 4.27E−08 | ✓ | | ✓ | ✓ | ✓ |
| 136207 | 2.84E−06 | | | | | |
| Total no.: | | 9 | 4 | 8 | 6 | 9 |

*Heterobasidion annosum* (white-rot)

| Protein ID | E-Value | JGI | NN | HMM | Phobius | Philius |
|---|---|---|---|---|---|---|
| 452336 | 2.81E−70 | | | | | |
| 442771 | 9.33E−58 | | | | | |
| 453182 | 1.25E−42 | ✓ | | ✓ | ✓ | ✓ |
| 439810 | 1.41E−38 | ✓ | | ✓ | ✓ | ✓ |
| 311280 | 1.72E−37 | ✓ | | ✓ | ✓ | ✓ |
| 456460 | 6.50E−35 | | | | | ✓ |
| 156655 | 6.64E−21 | ✓ | ✓ | ✓ | | |
| 50705 | 8.19E−21 | | | | | |
| 313519 | 3.81E−14 | ✓ | ✓ | ✓ | ✓ | ✓ |
| 458376 | 3.37E−13 | ✓ | ✓ | ✓ | ✓ | ✓ |
| 12711 | 4.26E−11 | ✓ | ✓ | ✓ | | |
| 312653 | 1.19E−10 | | | | | |
| 458375 | 1.37E−08 | ✓ | ✓ | ✓ | ✓ | ✓ |
| 50323 | 9.34E−08 | ✓ | | | | |
| 218303 | 1.15E−06 | ✓ | ✓ | ✓ | ✓ | |
| 439383 | 3.18E−06 | ✓ | ✓ | ✓ | ✓ | ✓ |
| Total no.: | | 11 | 7 | 10 | 8 | 8 |

*Postia placenta* (brown-rot)

| Protein ID | E-Value | JGI | NN | HMM | Phobius | Philius |
|---|---|---|---|---|---|---|
| 112407 | 1.59E−59 | | | | | |
| 32625 | 1.96E−59 | | | ✓ | | |
| 105326 | 5.92E−58 | | | | | |
| 32934 | 9.30E−55 | | | ✓ | | |
| 62058 | 3.40E−51 | | | | | |
| 87724 | 2.70E−50 | | | | | |
| 54109 | 1.39E−47 | | | | | |
| 46071 | 4.90E−47 | | | | | |
| 46909 | 1.57E−39 | ✓ | | ✓ | | ✓ |
| 23052 | 1.69E−35 | ✓ | | ✓ | | |
| 40396 | 4.61E−24 | | | | | |
| 56710 | 5.89E−23 | ✓ | ✓ | ✓ | ✓ | ✓ |
| 22746 | 1.10E−15 | ✓ | ✓ | ✓ | ✓ | |
| 58133 | 1.76E−10 | ✓ | ✓ | ✓ | ✓ | ✓ |
| 102649 | 1.76E−10 | ✓ | | ✓ | ✓ | ✓ |
| 26732 | 1.03E−09 | | | | | |
| 102563 | 8.71E−08 | | | ✓ | | |
| Total no.: | | 6 | 3 | 9 | 4 | 4 |

*Gloeophyllum trabeum* (brown-rot)

| Protein ID | E-Value | JGI | NN | HMM | Phobius | Philius |
|---|---|---|---|---|---|---|
| 38668 | 1.41E−67 | ✓ | ✓ | ✓ | ✓ | ✓ |
| 95824 | 5.49E−60 | | | | | |
| 40080 | 8.65E−52 | ✓ | | ✓ | | |
| 140449 | 9.97E−48 | ✓ | | ✓ | ✓ | ✓ |
| 93300 | 1.69E−40 | | | | | |
| 40143 | 2.32E−40 | ✓ | | ✓ | | |
| 140453 | 9.45E−39 | ✓ | ✓ | ✓ | ✓ | ✓ |
| 35107 | 2.92E−24 | | | | | |
| 140174 | 1.97E−23 | | | | | |
| 104708 | 1.70E−22 | | | | | |
| 108145 | 1.10E−15 | | | | | |
| 79748 | 9.80E−14 | | | | | |
| 137345 | 2.24E−10 | ✓ | ✓ | | | |
| 76666 | 2.84E−10 | ✓ | | ✓ | | ✓ |
| 76829 | 3.17E−10 | ✓ | ✓ | ✓ | ✓ | ✓ |
| 138935 | 1.85E−09 | ✓ | ✓ | ✓ | | ✓ |
| 74706 | 2.23E−08 | ✓ | ✓ | ✓ | ✓ | ✓ |
| 74260 | 5.89E−08 | ✓ | | ✓ | | ✓ |
| 63391 | 4.67E−07 | ✓ | ✓ | ✓ | | ✓ |
| 132534 | 5.12E−07 | ✓ | | ✓ | | ✓ |
| 30301 | 8.17E−07 | | | | | |
| 70195 | 1.00E−06 | ✓ | ✓ | ✓ | ✓ | ✓ |
| 75410 | 1.35E−06 | | | | | |
| 62491 | 1.75E−06 | | | | | |

TABLE I-continued

Flavoproteins in Secretomes of White-rot and Brown-rot Fungi

| | | | SignalP 3.0[d] | | | |
|---|---|---|---|---|---|---|
| Protein ID[a] | E-Value[b] | JGI[c] | NN | HMM | Phobius[e] | Philius[e] |
| 118402 | 4.77E−06 | ✓ | | ✓ | ✓ | ✓ |
| 67540 | 8.75E−06 | ✓ | ✓ | ✓ | | |
| 109378 | 8.96E−06 | | | | | |
| 43940 | 9.60E−06 | | | | | |
| Total no.: | | 16 | 12 | 14 | 7 | 11 |

[a] Identification number ascribed to protein by Joint Genome Institute (JGI).
[b] The E-value ("Expect Value") cutoff is set by JGI at the default of $1.0 \times 10^{-5}$. The E-value describes the number of hits to a query sequence one can "expect" to see by chance when searching a database of a particular size. This means that the lower the E-value, the higher is the "significance" of the match.
[c] Joint Genome Institute (JGI)
[d] SignalP version 3 (SignalP 3.0) uses both a hidden Markov model (HMM) and a neural network (NN) to predict whether a signal peptide sequence is present.
[e] Phobius employs a joint HMM embodying submodels for signal peptides and transmembrane segments. Philius is inspired by Phobius, and uses dynamic Bayesian networks to discriminate between three signal peptide and transmembrane configurations as it seeks to predict the location of the signal peptide cleavage site and/or the complete membrane-protein topology (Reynolds et al., 2008, PLoS Computational Biology, 4(11): e1000213).

Hemicellulases (e.g., xylanase) and cellulases are also present in the secretomes of basidiomycetes. Moreover, lignin domains in lignocellulosic plant materials are capable of adsorbing a number of extracellular fungal proteins. Since the dissociative activity of the auxiliary compound is not dependent upon any particular enzymatic activity, any of these extracellular fungal proteins—or analogs thereof—may serve as a protein auxiliary compound. The dissociative activity of the auxiliary compound is dependent upon the auxiliary compound being able to disrupt the intermolecular forces between substructures in lignin chains and/or those between lignin substructures and lignin depolymerase.

Quantitative estimates of the strengths of the intermolecular forces between substructures in interacting lignin chains were first made in our research group (Chen and Sarkanen, 2010, Phytochemistry 71:453-462). Indeed, despite a considerable world-wide effort during the past 30 years, no enzyme has yet been identified that is capable of degrading native lignin macromolecules. The enzymes investigated thus far—e.g., lignin peroxidase, manganese peroxidase, and laccase-mediator systems—that have been reported to be capable of degrading lignins are actually poised in their effects between cleaving and either polymerizing or repolymerizing macromolecular lignin chains (Wariishi et al., 1991, Biochem. Biophys. Res. Commun. 176:269-275; Hammel et al., 1993, J. Biol. Chem. 268: 12274-12281; Bourvonnais et al., 1998, Biochem. Biophys. Acta 1379:381-390). The enzymes previously studied, and the methods used to evaluate the enzymes, fail to disrupt the intermolecular forces that are responsible for the integrity of macromolecular lignin complexes. In some instances, these intermolecular noncovalent forces can approximate or exceed those leading to the stabilization of G-C base pairs in DNA double helices. No enzyme has yet been successfully employed to degrade lignins and disrupt these intermolecular noncovalent bonds, thereby enhancing conversion of lignocellulose to paper pulp or transformation of lignocellulose to liquid biofuels.

The recalcitrance of lignin domains in plant-cell walls has its origins in two commanding features of their physicochemical properties. First, most of the linkages between monomer units in lignin macromolecules are rather stable and hence difficult to cleave, either chemically or biochemically. Second, the noncovalent intermolecular interactions between substituted aromatic rings on the one hand, and cyclohexadienone residues on the other, in neighboring lignin chains lead to stabilization energies in the range of 7-11 kcal/mol each. These energies are so high that cleavage of inter-unit linkages in lignin macromolecules may not automatically liberate oligomeric degradation products from a lignin domain.

Whether partially degraded or not, individual lignin components cannot immediately dissociate from one another in solution around neutral pH because of these strong intermolecular interactions between them. Indeed, in many instances, further association between them is favored entropically; additional contributions to such effects may result from interactions between the lignin components and the lignin depolymerase enzyme. Suitable auxiliary compounds can annul such effects by competing with the interactions of the degraded lignin components toward one another and toward the lignin depolymerase.

Consequently, care should be exercised in selecting substrates for evaluating potential lignin depolymerase activity in lignin depolymerase assays. The intermolecular forces that modulate the process of degrading native lignin do not have a comparable effect when one uses lignin model compounds. For example, compounds structurally unrelated to lignin are not likely to be useful for predicting whether an enzyme should be functionally capable of degrading polymeric lignin substrates. The stabilization energies arising from the entirety of the intermolecular noncovalent interactions between even widely accepted lignin model compounds are much lower than those between lignin macromolecules. Even the configurations of synthetic lignins—e.g., those produced by dehydropolymerizing monolignols in vitro—will be less well-defined than those preserved in polymeric preparations conscientiously isolated from lignin domains in plant-cell walls. The degree of complementarity between interacting lignin chains will influence the stabilization energy created by the noncovalent interactions between them (Guan et al., 1997, Phytochemistry 45:911-918). Consequently, the discovery of these intermolecular interactions, and the recognition that overcoming the effects of these forces is involved in the overall degradation of lignin, create a new analytical framework for assessing the lignin degradation activity of the various compounds in lignin depolymerase assays.

Thus, in one aspect, the invention provides a method of depolymerizing lignin that generally involves contacting a lignin sample with a lignin depolymerase to at least partially cleave the lignin macromolecules, and then contacting the resulting cleavage products with an auxiliary compound that facilitates the dissociation of the degraded components from the other polymer chains and/or the lignin depolymerase. As used herein, a "lignin" sample refers to any sample that includes macromolecular lignin, regardless of whether the sample includes other natural or added components. Thus, a lignin sample may range from, for example, unprocessed biomass to partially pre-processed biomass—e.g., biomass that has undergone one or more pre-processing steps. Samples that are at least partially pre-processed need not have had any residual components from any pre-processing step removed to any degree. However, a lignin sample that has undergone at least partial pre-processing also can have had at least some of the residual components of any pre-processing step removed to any degree.

Significantly, in the method provided herein, the lignin sample can include native lignin—i.e., lignin in which the constituent biopolymers have not been extensively derivatized or modified with respect to their native configuration other than in regard to molecular weight.

The lignin depolymerase may be any enzyme capable of cleaving lignin macromolecules into lignin components. In many embodiments, the lignin depolymerase may be an enzyme expressed in the secretome of a white-rot fungus, a brown-rot fungus, or a bacterium. Exemplary white-rot fungi include, for example, *Phanerochaete chrysosporium*, *Trametes versicolor*, and *Heterobasidion annosum*. Exemplary brown-rot fungi include, for example, *Postia placenta*. A suitable exemplary lignin depolymerase enzyme expressed in the secretomes of such organisms include, for example, a flavin-dependent monooxygenase (e.g., salicylate hydroxylase or any enzyme listed in Table I), a peroxidase (e.g., a lignin peroxidase, a manganese-dependent peroxidase, versatile peroxidase), β-etherase, a laccase (e.g., a 'yellow' laccase or a 'blue' laccase from a white-rot fungus).

In particular embodiments, the lignin depolymerase includes an enzyme that catalyzes cleavage of the lignin macromolecules into smaller lignin components but does not catalyze the repolymerization of the degraded lignin components. In certain of these embodiments, the lignin depolymerase can include a flavin-dependent monooxygenase such as, for example, salicylate hydroxylase or any enzyme listed in Table I.

In other embodiments, the lignin depolymerase can include an enzyme that may, if given the opportunity, catalyze the repolymerization of the lignin components. In such embodiments, the dissociative activity of the auxiliary compound may reduce the repolymerization activity of the lignin depolymerase so that the balance between depolymerization and repolymerization favors depolymerization. In other cases, the method may benefit from some manner of sequestering the depolymerized and dissociated lignin components to favor lignin depolymerization. In other words, cleaved or degraded lignin components may be noncovalently bound to another auxiliary component in such a way as to prevent their (re)polymerization.

The auxiliary compound can be any compound that adsorbs to the lignin components and modulates the intermolecular forces described above, causing dissociation of the lignin components from the other lignin macromolecules and/or from the lignin depolymerase enzyme. Here again, the auxiliary compound can be a protein expressed in the secretome of a white-rot fungus, a brown-rot fungus, or a bacterium. As such, many auxiliary compounds can be enzymes possessing certain catalytic activities. However, as noted above, the native enzymatic activity of such auxiliary compounds is not required for the dissociative activity with respect to degraded lignin components. The unifying characteristic of the auxiliary compound is that it interacts noncovalently with the lignin components and/or the lignin depolymerase, disrupts the intermolecular forces between the lignin components and the lignin macromolecules and/or the lignin depolymerase, and thereby dissociates the lignin components from the macromolecular lignin complexes.

In certain embodiments, the auxiliary compound may be a member of the secretome of a fungus—i.e., be a secreted fungal protein. In some cases, the auxiliary compound may be known to be adsorbed by lignin domains in lignocellulosic plant materials. Thus, exemplary fungal proteins that can serve as an auxiliary compound can include, for example, enzymes such as a cellulase, a hemicellulase (e.g., xylanase), a protease, a glycoside hydrolase (e.g., a member of glycoside hydrolase family 61).

The auxiliary compounds described immediately above are all naturally-occurring molecules or macromolecules. Because the dissociative activity of the auxiliary compound is not dependent upon, for example, native enzymatic activity of certain exemplary auxiliary compounds, one can substitute a non-enzymatic analog for certain enzymatic auxiliary compounds. As stated above, the analog need only be capable of interacting with lignin components in such a way—e.g., by adsorption—as to overcome the intermolecular forces between the lignin components and other lignin macromolecules and/or the lignin depolymerase enzyme. Thus, in some embodiments, the auxiliary compound may be a synthetic, recombinant, and/or modified version of a natural auxiliary compound—e.g., an analog of, for example, a carbohydrate binding module.

Figure 2:
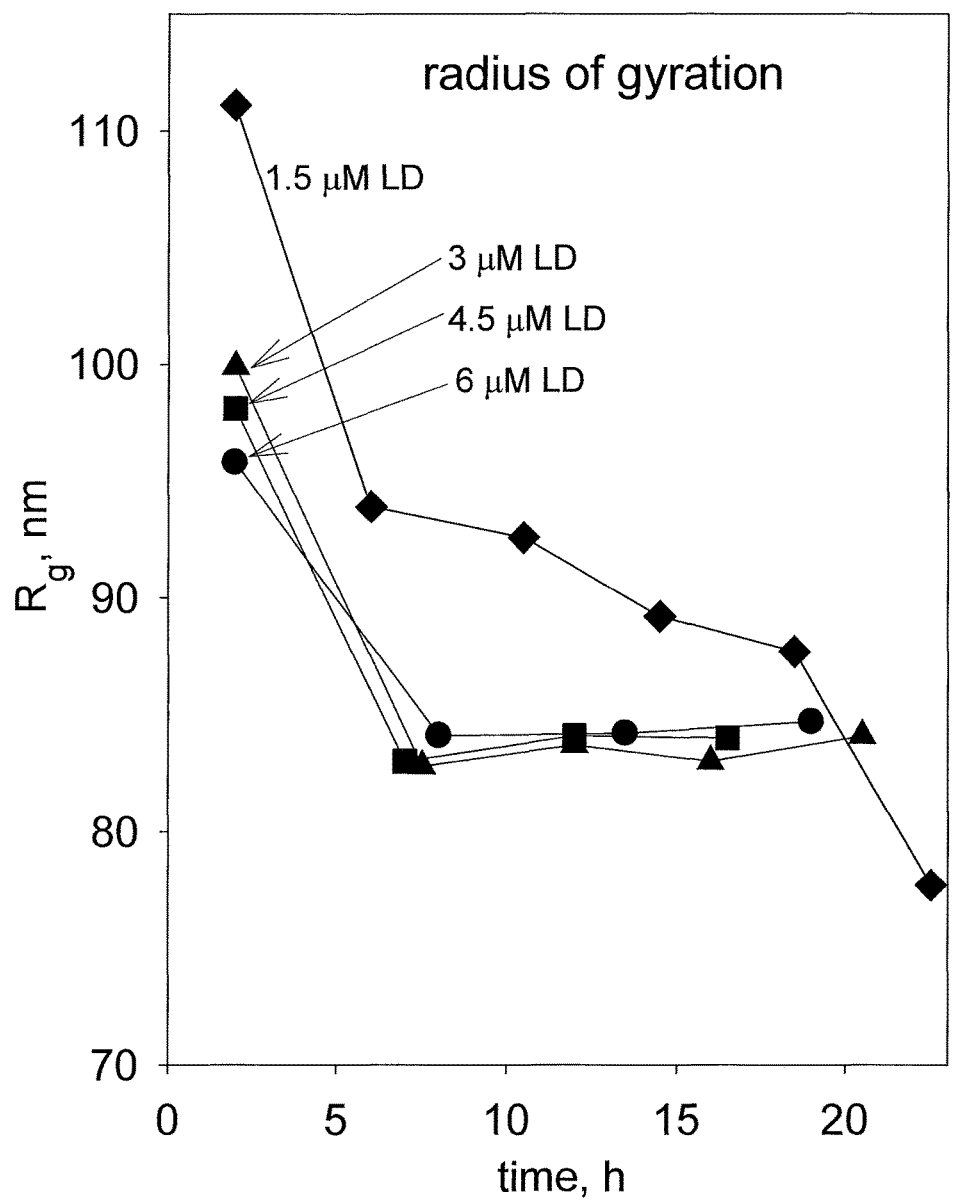
FIG. 2. Changes in radius of gyration of soluble native polymeric lignin preparation caused by lignin depolymerase at pH 6.3 in 25 mM phosphate containing 30 µM NADH.

The effects of an exemplary lignin depolymerase, the flavin-dependent monooxygenase, salicylate hydroxylase, on the apparent molecular weight of a soluble native polymeric lignin preparation at pH 6.3 are illustrated in FIG. 1. FIG. 2 shows that the radius of gyration decreases when native lignin is incubated in the presence of salicylate hydroxylase. A decrease in the radius of gyration indicated cleavage of the lignin macromolecules to smaller lignin components. FIG. 1, however, shows that the weight-average molecular weight increases over time after salicylate hydroxylase is added to the native lignin. Since the weight-average molecular weight of the substrate continues to increase after the radius of gyration has reached its asymptotic value, the observed effects result from two different physicochemical processes, cleavage of lignin macromolecules (causing the decrease in the radius of gyration) followed by association of degraded components (causing the increase in weight-average molecular weight).

The lower molecular weight components resulting from enzymatic lignin cleavage are, for entropic reasons, able to associate further than the macromolecules originally present in the native lignin employed here. The effect may be further enhanced by noncovalent interactions between the lignin components and the lignin depolymerase enzyme. Under the prevailing solution conditions at pH 6.3, the polymeric substrate largely consists of associated complexes composed of more than 20 individual lignin components.

Moreover, even though NADH is required for the native enzymatic activity of salicylate hydroxylase toward its natural substrate (salicylic acid), the cofactor is not needed for the activity of the enzyme toward native polymeric lignin substrates. Native lignin components can provide the reductive capacity of NADH needed by salicylate hydroxylase. Indeed, native lignin components can replace the reductive capacity of NADH for the native salicylate hydroxylation activity hydroxylating salicylate.

Figure 3:
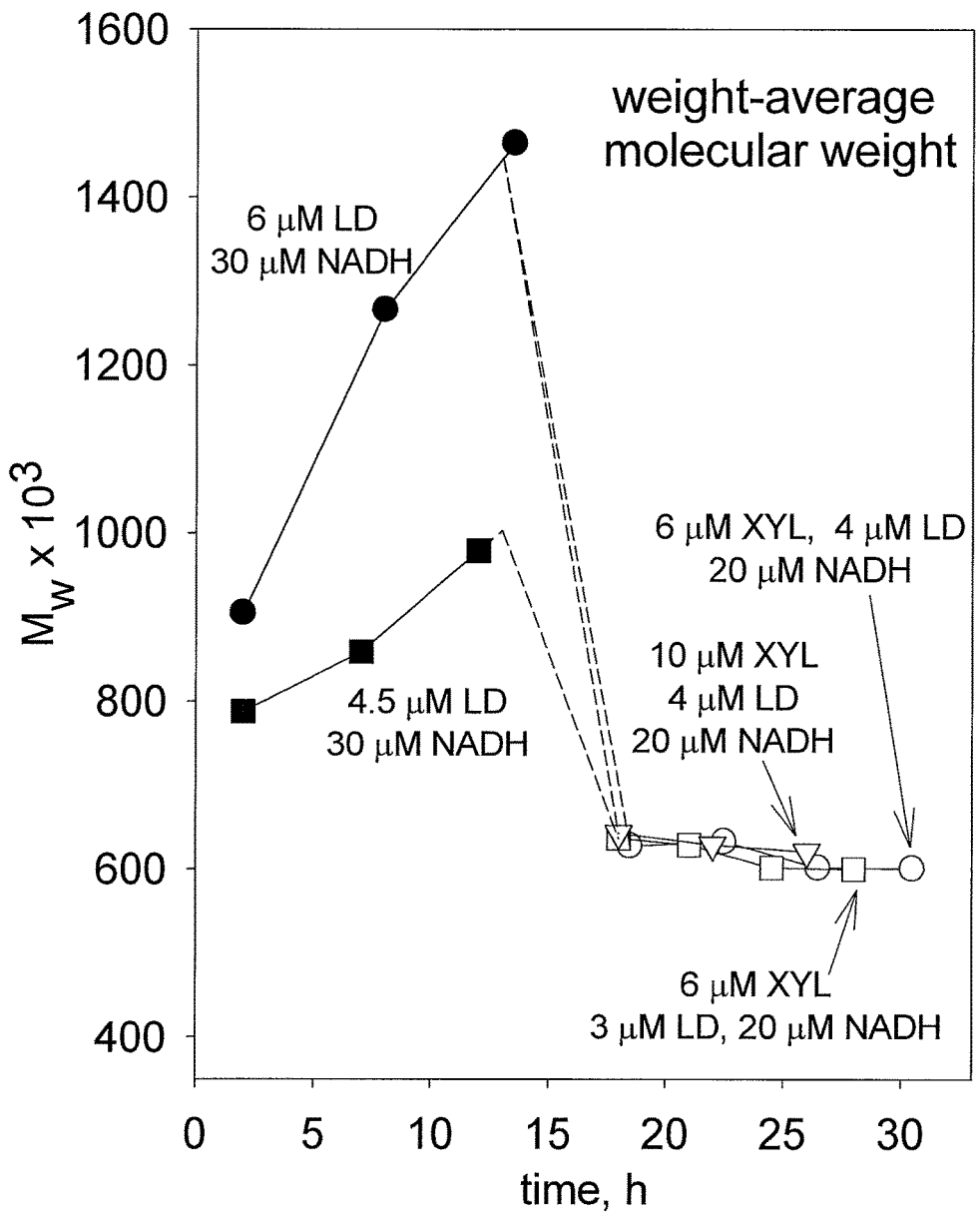
FIG. 3. Xylanase-generated changes in weight-average molecular weight of soluble native polymeric lignin preparation (open symbols) after 13 hours incubation in presence of lignin depolymerase (closed symbols) at pH 6.3 (0.025 M phosphate).
Figure 4:
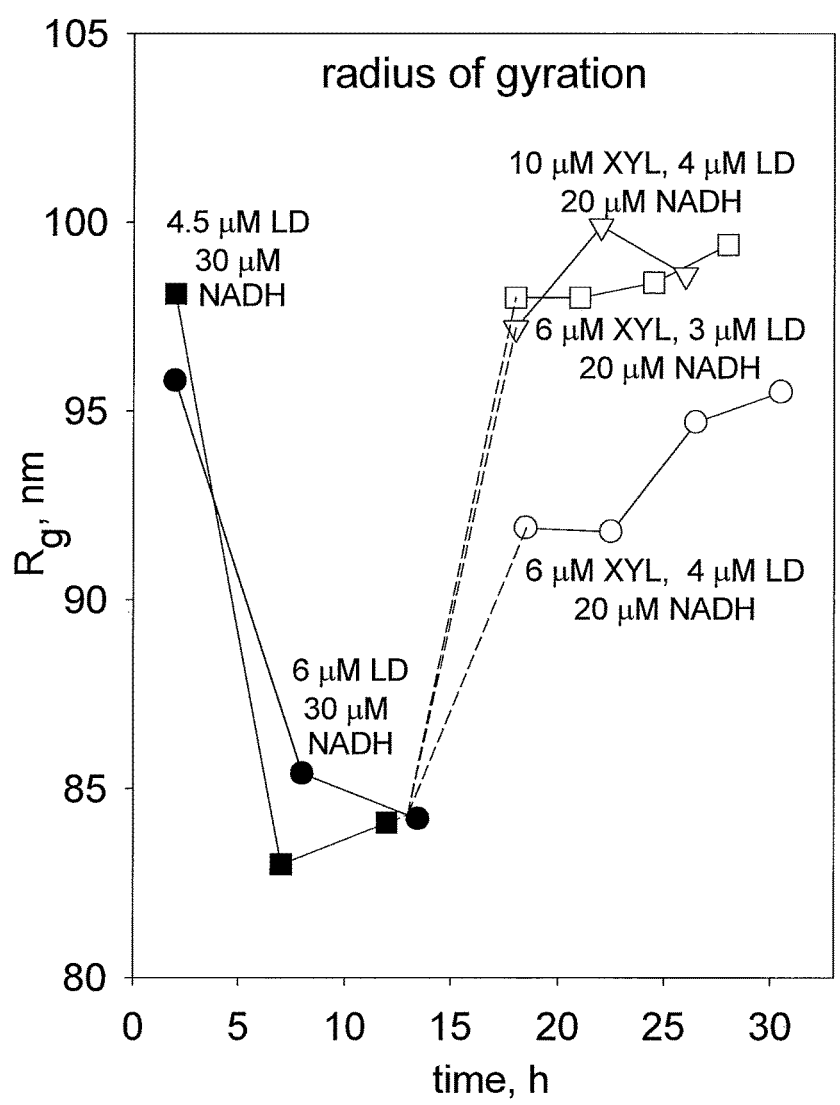
FIG. 4. Xylanase-generated changes in radius of gyration of soluble native polymeric lignin preparation (open symbols) after 13 hours incubation in presence of lignin depolymerase (closed symbols) at pH 6.3 (0.025 M phosphate).
Figure 6:
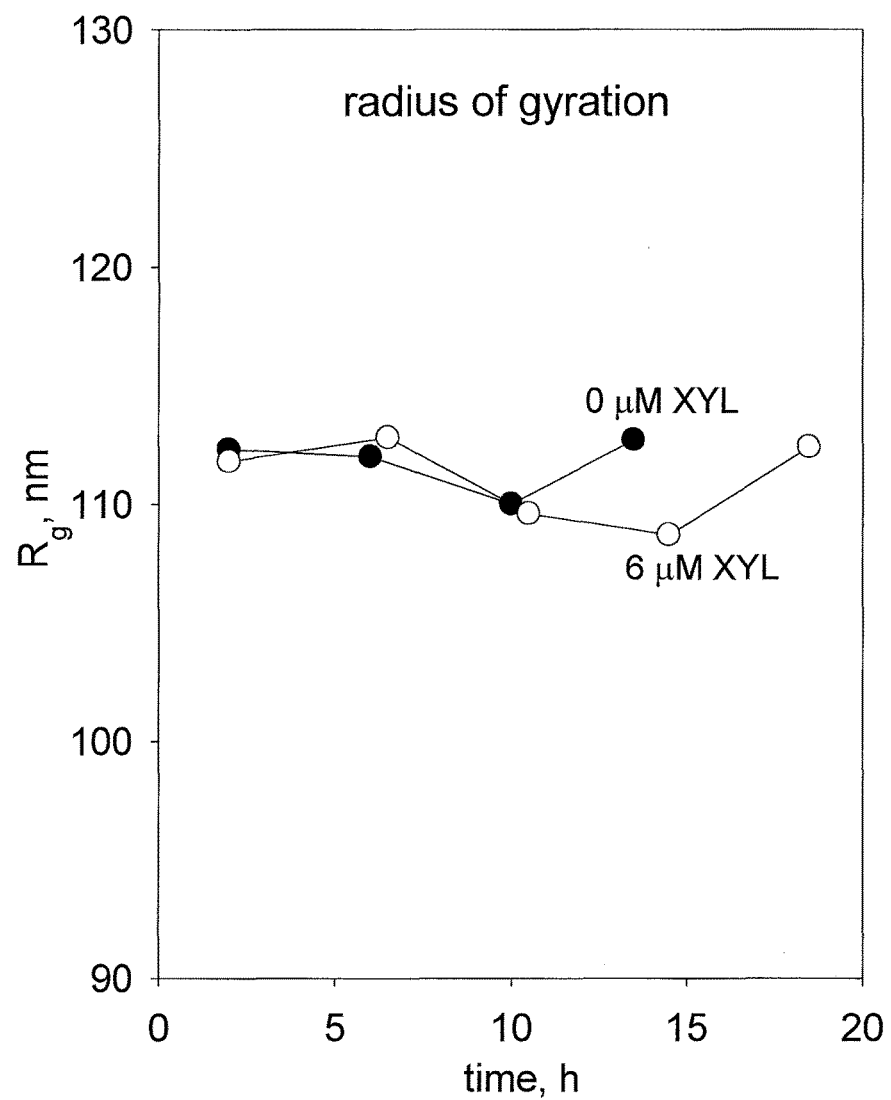
FIG. 6. Effect of xylanase alone on radius of gyration of soluble native polymeric lignin preparation at pH 6.3 (0.025 M phosphate).
Figure 7:
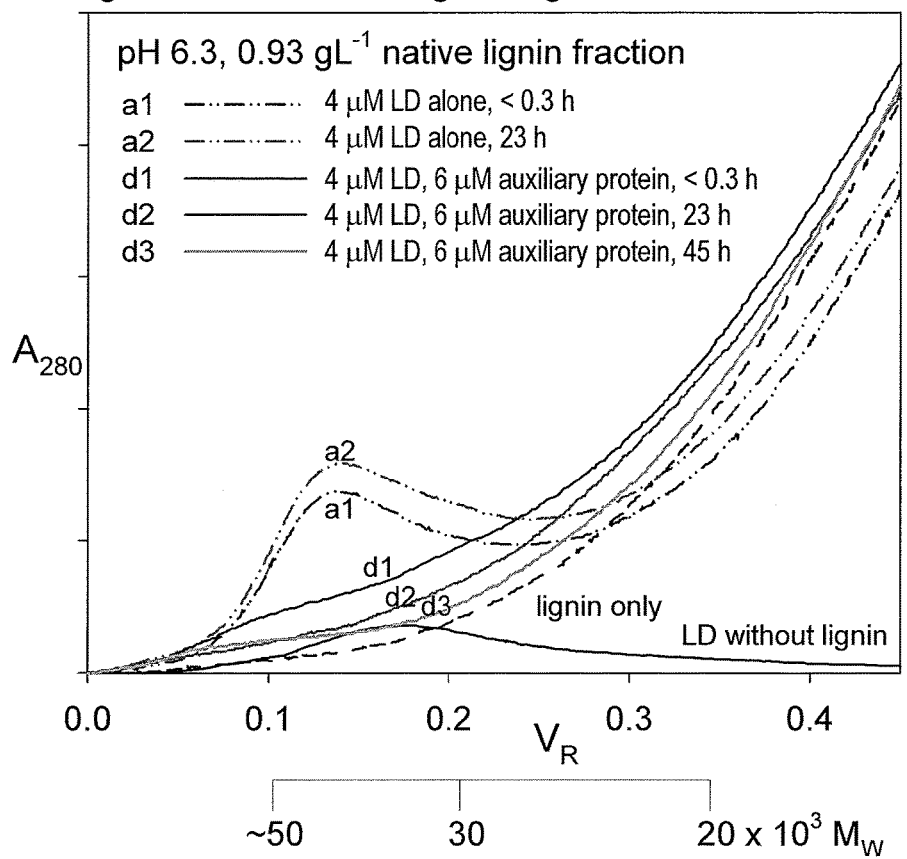
FIG. 7 shows the interactions of native polymeric lignin components with salicylate hydroxylase (LD) in the presence or absence of xylanase acting as an auxiliary compound. (0.0-0.45 $V_R$ segments of Sephadex G100/aqueous 0.10 M NaOH profiles after incubation times indicated.)

The dissociation of the associated complexes formed after macromolecular lignin cleavage is illustrated in FIG. 3 and FIG. 4. As shown in FIG. 3, both 6 μM and 10 μM xylanase cause rapid dissociation of the lignin complexes that are spontaneously assembled as shown in FIG. 1. The weight-average molecular weight of the partially degraded lignin sample generated by the activity of 6 μM lignin depolymerase falls to almost the same value whether 6 μM or 10 μM xylanase is added to the solution (which is diluted 1.5-fold in the process depicted in FIG. 3). On the other hand, the radius of gyration, which tends to increase under these circumstances, attains an appreciably higher value in the presence of 10 μM rather than 6 μM xylanase (FIG. 4) in the 1.5-fold diluted solution. Xylanase alone has no discernible effect on the weight-average molecular weight (FIG. 5) or the radius of gyration (FIG. 6) of the native lignin substrate. Indeed, this lignin substrate contains no detectable monosaccharide residues as a result of the fractionation procedure used in its preparation. Thus, the xylanase may act in an auxiliary capacity by competing with the interactions of the partially degraded lignin components toward one another and/or toward the lignin depolymerase. Size-exclusion chromatographic analysis under alkaline conditions (aqueous 0.10 M NaOH/Sephadex G100) has confirmed that xylanase results in dissociation of the lignin depolymerase from the high molecular weight lignin components (FIG. 7).

Figure 8:
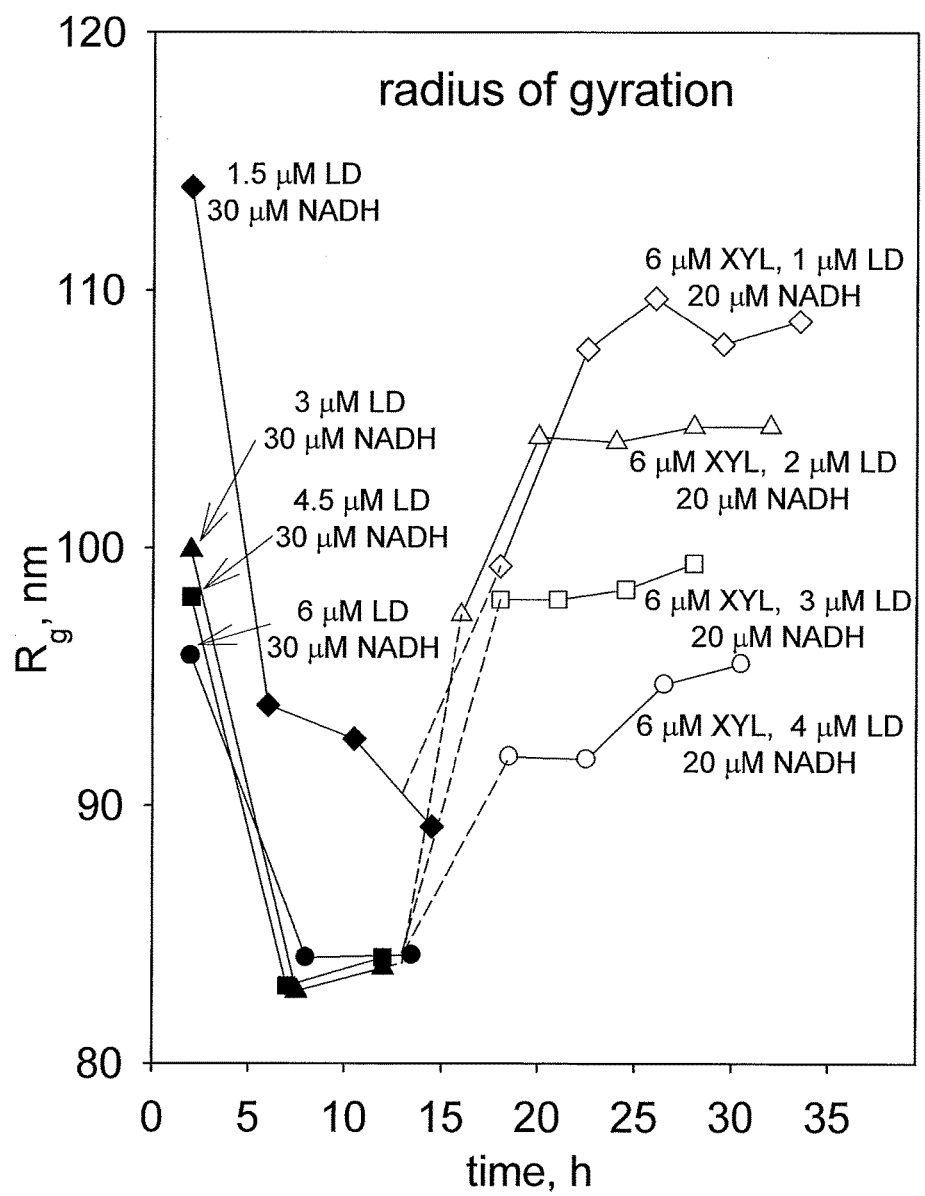
FIG. 8. Xylanase-generated changes in radius of gyration of soluble native polymeric lignin preparation (open symbols) after 13 hours incubation in presence of lignin depolymerase (closed symbols) at pH 6.3 (0.025 M phosphate).

Surprisingly, the radius of gyration of the partially cleaved lignin substrate tends to approach its original value—i.e., before exposure to lignin depolymerase—after introducing the auxiliary compound (e.g., xylanase) into solution, especially when the lignin-depolymerase concentration is low (FIG. 8). Without wishing to be bound exclusively by any particular theory, it may be that a memory of the original configuration, which may be embodied in the associated complexes of the substrate, can survive lignin-depolymerase-catalyzed cleavage of the native lignin components. Alternatively, the consecutive physicochemical effects of the lignin depolymerase and auxiliary compound could be influenced by conformational changes in the substrate components. Thus, the rapid initial reduction in radius of gyration may be an outcome of noncovalent interactions with the lignin depolymerase, which may result in more compact (and more rigid) conformations of the individual lignin components that lead to enhancements in the degree of association between them. The more compact conformations may then promote the slower but dramatic increase in substrate molecular weight that occurs in the presence of higher lignin depolymerase concentrations (see, e.g., FIG. 9, 6 µM LD, 0-13 hours). The rapid decrease in substrate molecular weight upon the introduction of xylanase may then arise from competition on the part of the glycoside hydrolase (acting simply as an auxiliary compound) in disrupting the prevailing noncovalent interactions between the lignin components and lignin depolymerase or other lignin components.

Figure 9:
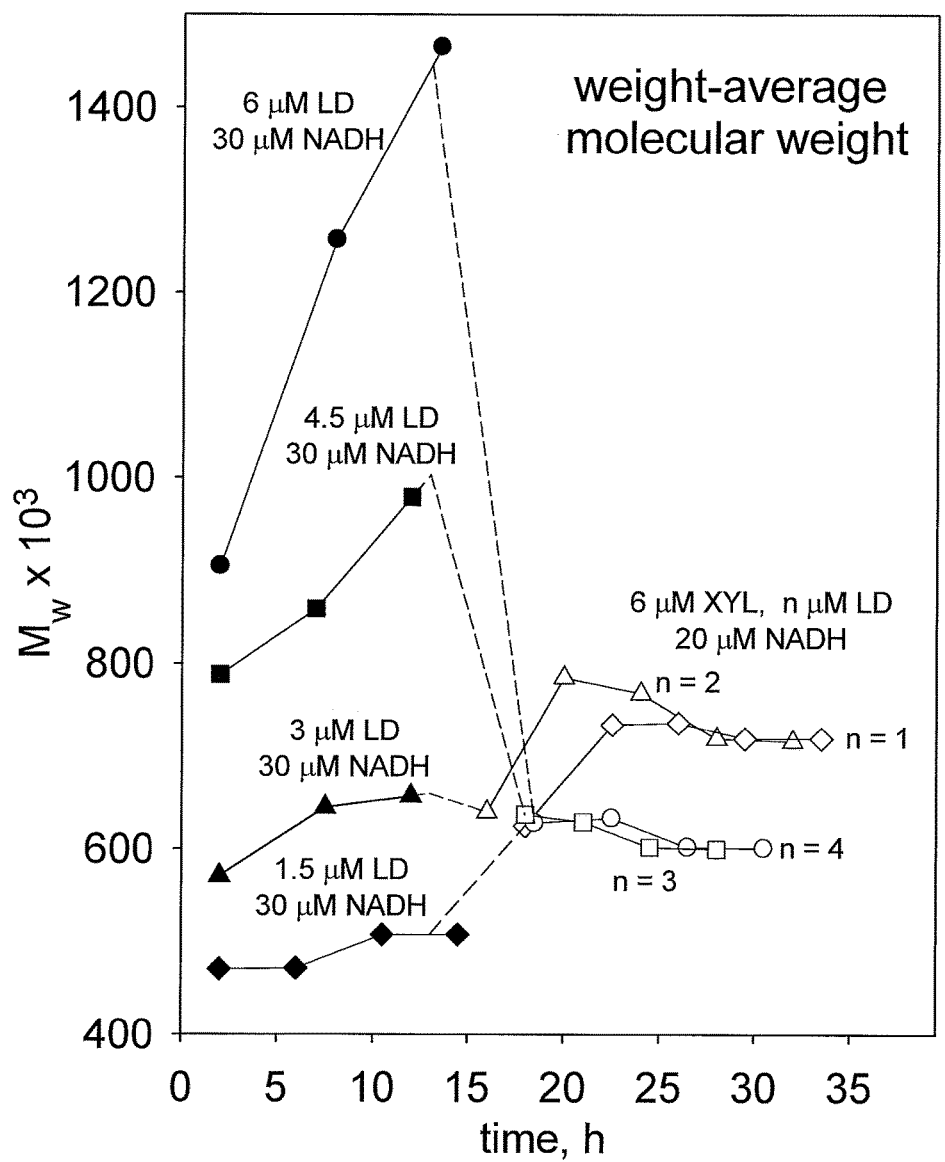
FIG. 9. Xylanase-generated changes in weight-average molecular weight of soluble native polymeric lignin preparation (open symbols) after 13 hours incubation in presence of lignin depolymerase (closed symbols) at pH 6.3 (0.025 M phosphate).
Figure 10:
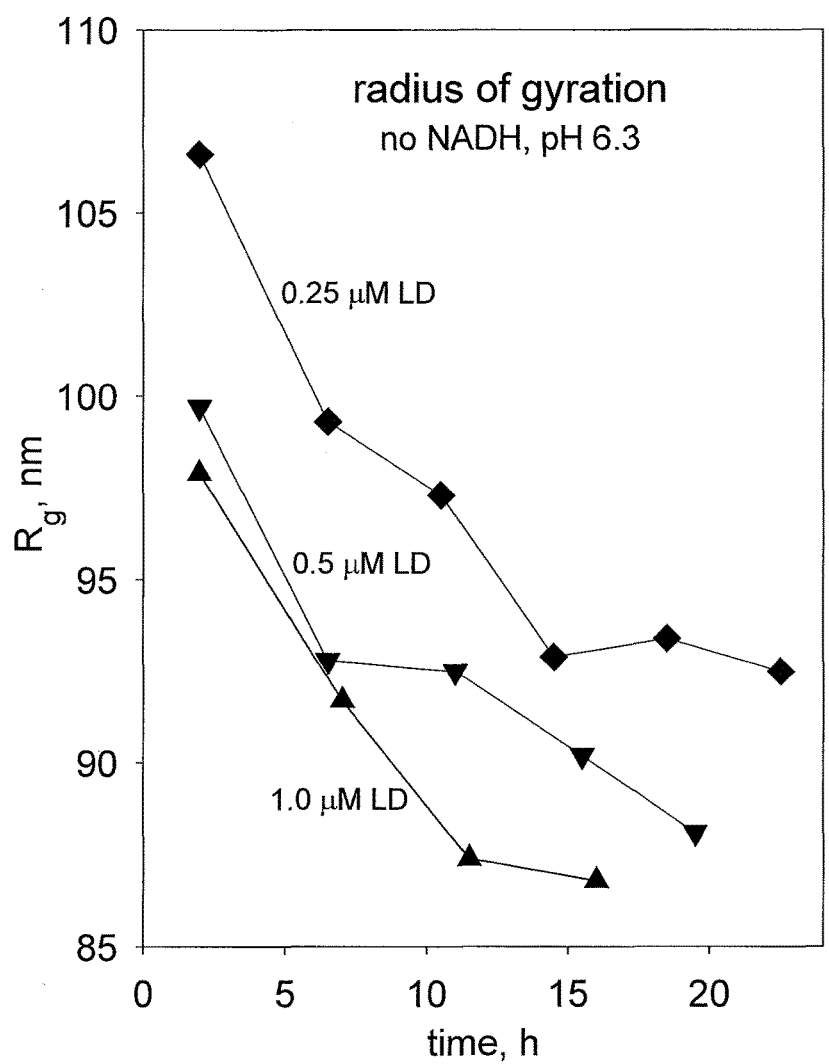
FIG. 10. Changes in radius of gyration of soluble native polymeric lignin preparation caused by low concentrations of lignin depolymerase without NADH at pH 6.3 in 25 mM phosphate.
Figure 11:
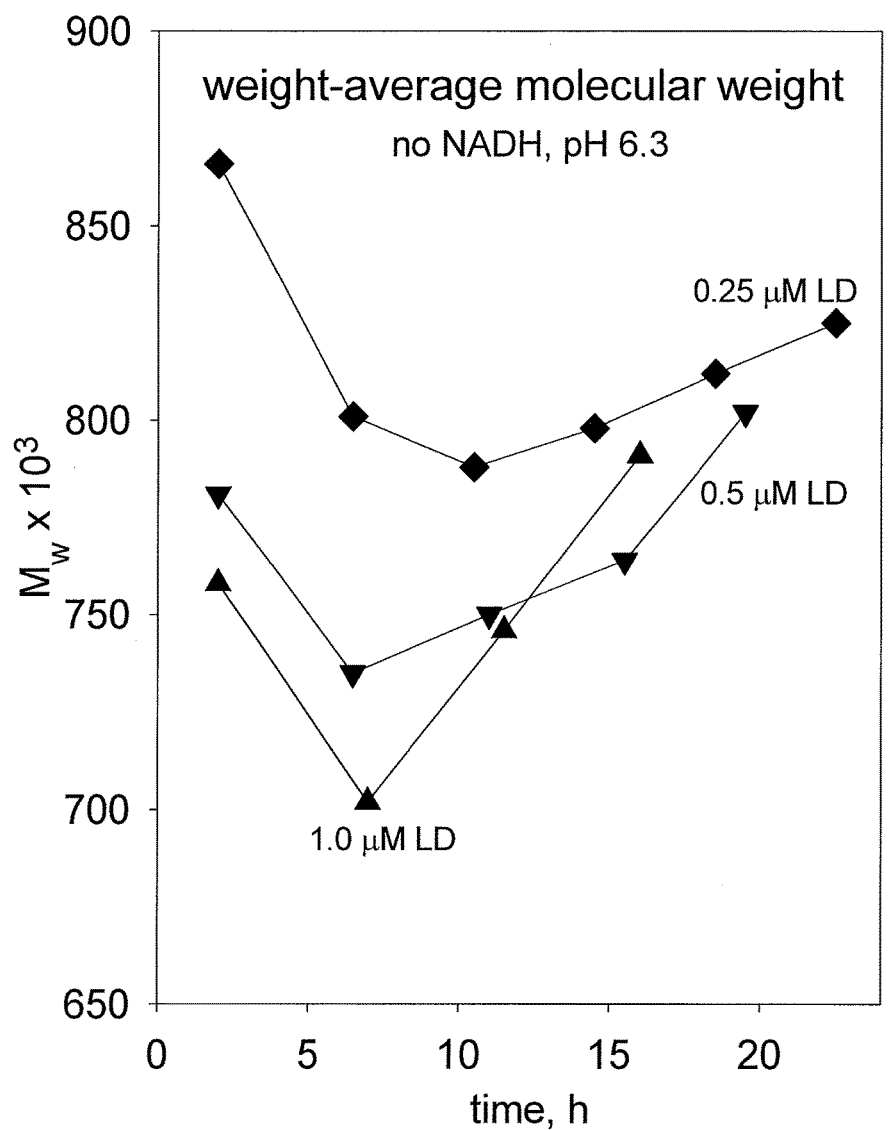
FIG. 11. Changes in weight-average molecular weight of soluble native polymeric lignin preparation caused by low concentrations of lignin depolymerase without NADH at pH 6.3 in 25 mM phosphate.

Nevertheless, the data in FIG. 9 indicate that processes other than conformational changes are occurring. The changes in radius of gyration and weight-average molecular weight of the native lignin substrate reflect complicated relationships with respect to each other that are governed by interactions with the lignin depolymerase and auxiliary compound under a range of conditions. A flavin-dependent monooxygenase such as salicylate hydroxylase traditionally requires NADH for its activity toward its natural monomeric substrate, salicylate. Nevertheless, native lignin can furnish the necessary reductive capacity when NADH is absent. Under such conditions, the relative rates of the steps in the catalytic cycle of the enzyme may be altered, but any impact on the overall process of enzymatic catalysis will depend, at least in part, on whether the velocity of the rate-limiting step is affected. The results obtained in solutions containing 0.25-1.0 µM lignin depolymerase without NADH at pH 6.3 reveal a decisive relationship between the radius of gyration and the weight-average molecular weight of this native lignin preparation (FIG. 10 and FIG. 11). The radius of gyration falls markedly (FIG. 10), although more slowly than in the presence of NADH (FIG. 2). Concomitantly, the molecular weight of the substrate now undergoes an initial reduction before beginning to rise as a result of intermolecular association between the degraded components (FIG. 11). Thus, lignin depolymerase does indeed cleave the individual lignin components before they start associating to form higher molecular weight complexes.

In the methods described herein, the degraded lignin components may be exposed to the effects of the auxiliary compound as they are produced by the cleavage of the native lignin macromolecules or at any time thereafter. Thus, in some embodiments, the lignin may be contacted with a mixture of the lignin depolymerase and the auxiliary compound. In other embodiments, the lignin may be contacted first with the lignin depolymerase, the resulting solution being allowed to incubate for any amount of time, prior to the onset of precipitation, before introducing the auxiliary component.

Figure 12:
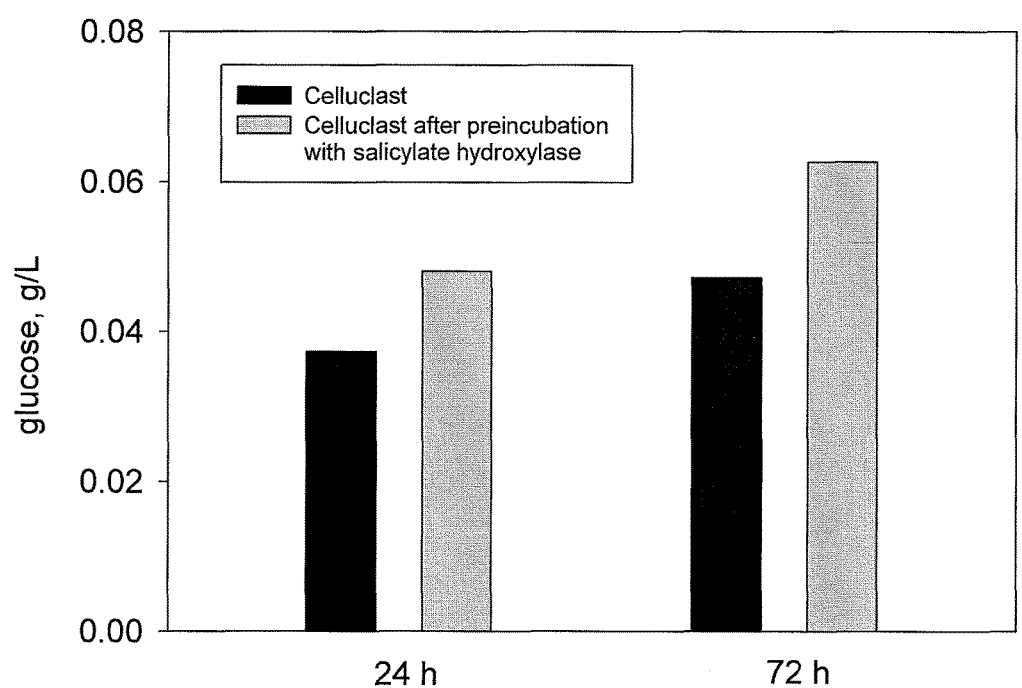
FIG. 12. Saccharification of wood meal by cellulase with and without lignin depolymerase pretreatment. 0.036 g wood meal in 12 mL phosphate at pH 6.3 containing 0.02% sodium azide and 10% (w/w g wood) CELLUCLAST (Novozymes A/S, Bagsvaerd, Denmark) with and without 13 hours preincubation in presence of 6 µM salicylate hydroxylase.

While the lignin-dissociating effect of the auxiliary compound does not require an enzymatic auxiliary compound to exhibit its native enzymatic activity, in some of these embodiments an auxiliary compound may exhibit enzymatic activity. Thus, for example, in embodiments in which the auxiliary compound includes a cellulase or a hemicellulase, the auxiliary compound may assist in lignin dissociation and also catalyze hydrolysis of cellulose or hemicellulose in the sample. In some of these embodiments, it may be sufficient to simply provide an amount of an enzymatic auxiliary compound that is enough to allow the auxiliary compound to perform both its lignin dissociating auxiliary function and its enzymatic function. FIG. 12 shows an increase in saccharification of Jack pine wood meal by the cellulase CELLUCLAST (Novozymes A/S, Bagsvaerd, Denmark) after pre-incubation with the lignin depolymerase, salicylate hydroxylase.

In certain aspects, the invention provides a method that generally includes, simply, contacting digested lignin with an auxiliary compound to facilitate the dissociation of cleaved lignin components from other lignin macromolecules.

Thus, during simultaneous treatment of lignocellulose with lignin depolymerase and cellulase, the latter enzyme may fulfill the dual functions of facilitating dissociation of the cleaved lignin components and engendering saccharification of polysaccharides.

In summary, we have demonstrated that two distinct physicochemical processes are involved in biochemical lignin depolymerization. The first results in the enzymatic cleavage of lignin macromolecules, while the second involves the dissociation of the modified lignin components from associated lignin complexes or domains by a proteinaceous auxiliary compound.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Assay Substrate

The definitive substrate for an enzyme that exhibits true lignin depolymerase activity would be a polymeric lignin sample derived with minimal chemical modification from a native lignin preparation. Preferably, such a lignin substrate will remain sufficiently soluble during the assay that complications arising from heterogeneous solution conditions can be avoided. Then classical light scattering measurements may be employed to determine how the (weight-average) molecular weight, Mw, and (z-average) radius of gyration, Rg, of the native lignin substrate change as a result of lignin depolymerase activity.

The simplest approach entails the selection of a standard milled-wood lignin from a softwood as the starting material. The milled-wood lignin is isolated by extraction with aqueous 96% dioxane in the customary way from the appropriate extractive-free wood meal. The crude product is purified by dissolving in (9:1:4 v/v/v) pyridine-acetic acid-water and extracting the resulting solution with chloroform. After complete solvent removal, the residue is redissolved in (2:1 v/v) 1,2-dichloroethane-ethanol and precipitated in ether (Lundquist et al., 1977, Svensk Papperstidn. 80(5):143-144).

The parent milled-wood lignin is ultrafiltered exhaustively in aqueous 0.10 M NaOH in turn through 30,000 and 10,000 nominal molecular weight cutoff membranes (Amicon YM30 and YM10, respectively; Millipore Corp., Billerica, Mass.). In each case, the time-course for ultrafiltration should be extended to allow dissociation of the retained macromolecular lignin complexes to occur (Contreras et al., 2008, Biomacromolecules 9:3362-3369) so that the individual components released may have the opportunity of passing through the membrane being used. When the permeate has become colorless, the sodium hydroxide in the retentate is removed by continuing the ultrafiltration process with distilled water and then triply distilled water until the pH reaches 7.0-7.5. The neutralized retentate solution is centrifuged to remove any precipitate (<10% of the original lignin in the fraction), and the supernatant with the dissolved milled-wood lignin substrate is stored in a TEFLON bottle (Berghof/America, Coral Springs, Fla.) under nitrogen.

Rayleigh Light Scattering.

The determination of weight-average molecular weight (Mw) and (z-average) radius of gyration (Rg) for the native lignin substrate involves extrapolation of the pertinent data to c=0 g/L in both cases (Chen, Y.-r., Sarkanen, S., Wang, Y.-Y. 2012. Lignin-Degrading Enzyme Activities. In M. E. Himmel, Ed., Methods in Molecular Biology: Biomass Conversion; Humana Press. Chapter 21, pp. 251-268). The substrate solutions in aqueous buffer are each passed through a 1.0 μm porous PTFE membrane (Pall Life Science, TF-1000, 13 mm diameter) prior to being introduced with a syringe pump into the flow-cell of a Wyatt DAWN HELEOS light-scattering photometer equipped with a 780 nm laser light source. Light scattering detectors (half fitted with interference filters to provide a means of correcting for fluorescence) are placed in a plane at 18 different angles around the position of the scattering volume in the flow-cell.

The values of Mw and Rg are determined from the intensity of the light scattered at each angle θ (Wyatt, 1993, Anal. Chim. Acta 272:1-40) through calculations that involve the refractive index of the buffer solution, and the refractive index increment at 780 nm of the dissolved substrate. The effect of solution absorbance upon the incident light intensity may be determined from the forward laser monitor signal intensities when the substrate solution and buffer alone, respectively, occupy the flow cell.

After various incubation times, assay solutions containing the native lignin fraction and enzyme possessing lignin depolymerase (LD) activity are diluted to create, in each case, a series of solutions with successively decreasing substrate concentrations. These are consecutively introduced into the DAWN HELEOS light-scattering flow-cell in order of increasing substrate concentrations.

As a given set of solutions is being analyzed, the scattered light intensities at angles θ change appreciably with time because of the impact of the enzyme on the native lignin substrate. Such effects would compromise a traditional Zimm-plot analysis of the data. The matter is better handled through the Debye formalism, from which the weight-average molecular weight and radius of gyration for the substrate can be determined in the standard way by extrapolating the appropriate quantities to zero weight-concentration.

The radius of gyration embodies a much weaker dependence on the refractive index increment (dn/dc) of the substrate than the weight-average molecular weight. Consequently, if it is suspected that the substrate dn/dc changes during its transformation into products, or if it is difficult to ascertain the impact of the enzyme on the overall differential refractive index of the assay solution, the radius of gyration is the preferred parameter for monitoring the effects of enzyme-catalyzed cleavage of lignin macromolecules.

Example 1

LD-catalyzed changes in weight-average molecular weight of soluble native polymeric lignin (1.4 g/L) preparation were assessed in the presence of 30 μM NADH at pH 6.3 (0.025 M phosphate). Salicylate hydroxylase (6 μM, 4.5 μM, 3 μM, or 1.5 μM) from *Pseudomonas* spp. (Sigma-Aldrich, St. Louis, Mo., cat. No. S2907) was used as an exemplary lignin depolymerase. Results are shown in FIG. 1.

Example 2

LD-catalyzed changes in apparent radius of gyration of soluble native polymeric lignin (1.4 g/L) preparation were assessed in the presence of 30 μM NADH at pH 6.3 (0.025 M phosphate). Salicylate hydroxylase (6 μM, 4.5 μM, 3 μM, or 1.5 μM) from *Pseudomonas* sp. (Sigma-Aldrich, St. Louis, Mo., cat. No. S2907) was used as an exemplary lignin depolymerase. Results are shown in FIG. 2.

Example 3

Xylanase-generated changes in soluble native polymeric lignin (0.93 g/L) preparation (open symbols) were assessed after 13 hours incubation in the presence of either 4.5 μM or 6 μM salicylate hydroxylase (Sigma-Aldrich, St. Louis, Mo., cat. No. S2907) at pH 6.3 (0.025 M phosphate). Xylanase (XYL) concentrations (6 μM or 10 μM) are based on the molecular weight of the exemplary proteinaceous auxiliary compound xylanase from *Trichoderma viride* (Sigma-Aldrich, St. Louis, Mo., cat. No. X3876). Changes in weight-average molecular weight are shown in FIG. 3; changes in radius of gyration are shown in FIG. 4.

Example 4

Figure 5:
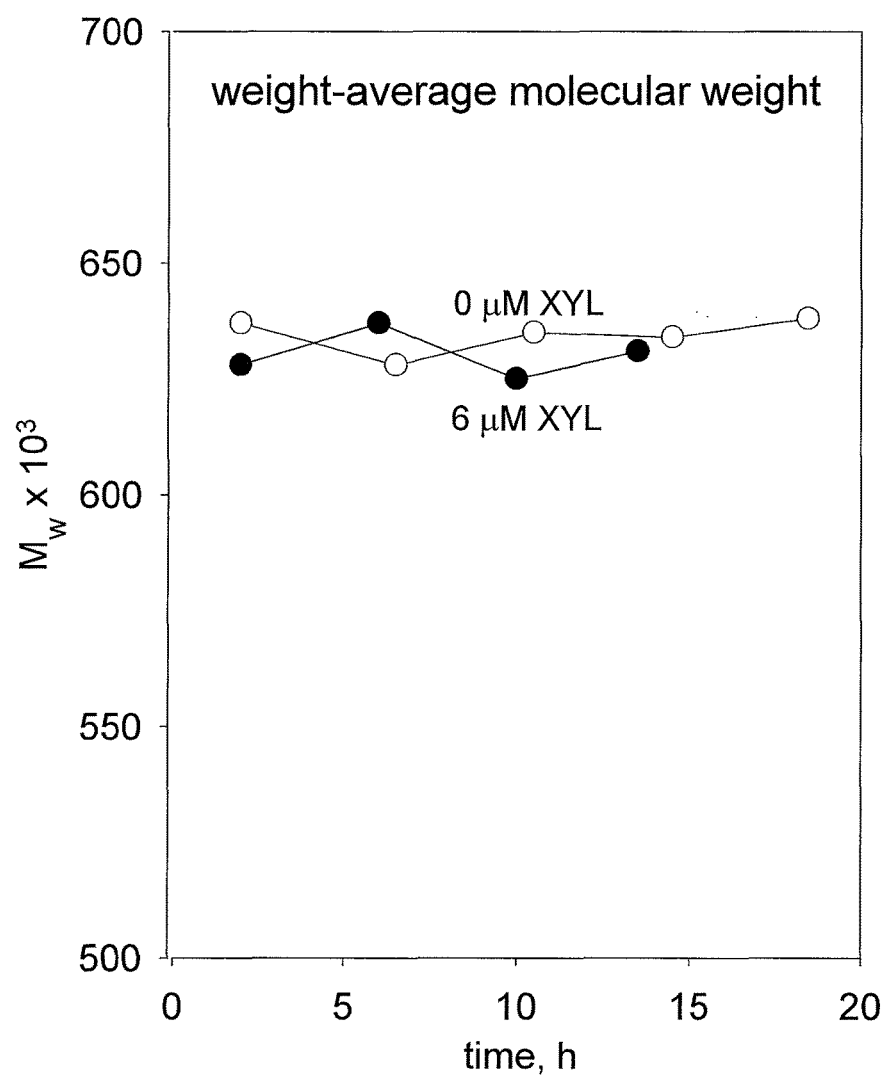
FIG. 5. Effect of xylanase alone on weight-average molecular weight of soluble native polymeric lignin preparation at pH 6.3 (0.025 M phosphate).

Effect of xylanase alone on soluble native polymeric lignin preparations (0.93 g/L) were assessed after incubation with or without xylanase. Xylanase (XYL) concentration (6 μM) is based on the molecular weight of the exemplary proteinaceous auxiliary compound xylanase from *Trichoderma viride* (Sigma-Aldrich, St. Louis, Mo., cat. No. X3876) Changes in weight-average molecular weight are shown in FIG. 5; changes in radius of gyration are shown in FIG. 6.

Example 5

Interactions of native polymeric lignin components with lignin depolymerase (LD, salicylate hydroxylase, Sigma-Aldrich, St. Louis, Mo.) in absence and presence of an auxiliary protein (xylanase, Sigma-Aldrich, St. Louis, Mo.) at pH 6.3 in 25 mM phosphate are illustrated in FIG. 7. (0.0-0.45 $V_R$ segments of Sephadex G100/aqueous 0.10 M NaOH elution profiles after incubation times indicated.)

Example 6

Xylanase-generated changes in soluble native polymeric lignin (0.93 g/L) preparations (open symbols) were assessed after 13 hours incubation in presence of 1.5 μM, 3.0 μM, 4.5 μM, or 6 μM salicylate hydroxylase (Sigma-Aldrich, St. Louis, Mo., cat. No. 52907) at pH 6.3 (0.025 M phosphate). Xylanase (XYL) concentration (6 μM) is based on the molecular weight of the exemplary proteinaceous auxiliary compound xylanase from *Trichoderma viride* (Sigma-Aldrich, St. Louis, Mo., cat. No. X3876). Changes in radius of gyration are shown in FIG. 8; changes in weight-average molecular weight are shown in FIG. 9.

Example 7

LD-catalyzed changes in soluble native polymeric lignin preparation (1.4 g/L) were assessed during incubation with low concentrations (0.25 μM, 0.5 μM and 1.0 μM) of salicylate hydroxylase in the absence of NADH at pH 6.3 (0.025 M phosphate). Variations in radius of gyration are shown in FIG. 10; variations in weight-average molecular weight are shown in FIG. 11. The salicylate hydroxylase from *Pseudomonas* sp. (Sigma-Aldrich, St. Louis, Mo., cat. No. 52907) was used as an exemplary lignin depolymerase.

Example 8

The effects of salicylate hydroxylase on cellulase-catalyzed saccharification of lignocellulose (in the form of Jack pine wood meal) were investigated according to NREL Laboratory Analytical Procedure, NREL/TP-510-42629, Enzymatic Saccharification of Lignocellulosic Biomass, with slight modifications. Each vial contained 0.036 g Jack pine sapwood meal (which had been subjected to acetone extraction) in 8 mL 0.025 M phosphate buffer (pH 6.3) containing 0.02% sodium azide in the absence or presence of (6 μM) salicylate hydroxylase. The vials were kept at room temperature on an orbital shaker overnight (13 hours). A volume of 4 mL phosphate buffer was then introduced into each vial with or without the addition of 3 μL CELLU-CLAST 1.5 L (Novozymes A/S, Bagsvaerd, Denmark), which corresponded to 10% w/w per g biomass.

After 24 hours and 72 hours, respectively, an aliquot (~1 mL) from each vial was filtered through a 0.2 μm syringe filter (Whatman Anotop 10, GE Healthcare Biosciences, Pittsburgh, Pa.) and subjected to monosaccharide analysis according to the standard NREL HPLC procedure (NREL/TP-510-42618, Determination of Structural Carbohydrates and Lignin in Biomass) using an Agilent system with a refractive index detector. A Bio-Rad Aminex HPX-87P column (Bio-Rad Laboratories, Inc., Hercules, Calif.) at 80° C.-85° C. protected by a Micro-Guard (Carbo-P) guard column was used. Results are shown in FIG. 12.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   contacting a lignin sample with an isolated flavin-dependent monooxygenase and forming at least partially degraded lignin; and
   contacting the lignin sample with an auxiliary compound that disrupts noncovalent interaction between the at least partially degraded lignin and the flavin-dependent monooxygenase.

2. The method of claim 1 wherein the lignin sample comprises native lignin.

3. The method of claim 1 wherein the isolated flavin-dependent monooxygenase is expressed in the secretome of a fungus or expressed in a bacterium.

4. The method of claim 3 wherein the fungus is a white-rot fungus or a brown-rot fungus.

5. The method of claim 4 wherein the flavin-dependent monooxygenase is salicylate hydroxylase, salicylate monooxygenase, 4-hydroxybenzoate monooxygenase, 4-hydroxyphenylacetate monooxygenase, melilotate monooxygenase, imidazoleacetate monooxygenase, orcinol monooxygenase, phenol monooxygenase, kynurenine monooxygenase, 2,6-dihydroxypyridine monooxygenase, 4-hydroxyphenylacetate monooxygenase, taxifolin monooxygenase, 2,4-dichlorophenol monooxygenase, 3-hydroxybenzoate monooxygenase, 4-aminobenzoate monooxygenase, anthranilate monooxygenase, anhydrotetracycline monooxygenase, anthraniloyl-CoA monooxygenase, 2-hydroxybiphenyl monooxygenase, pentachlorophenol monooxygenase, benzoyl-CoA monooxygenase, 3-hydroxyphenylacetate monooxygenase, 4-hydroxybenzoate monooxygenase, 4-methyl-5-nitrocatechol monooxygenase, 4-aminobenzoate monooxygenase, or 2-octaprenyl-6-methoxyphenol monooxygenase.

6. The method of claim 1 wherein the lignin sample is contacted with the flavin-dependent monooxygenase and the auxiliary compound simultaneously.

7. The method of claim 1 wherein the lignin sample is contacted with the flavin-dependent monooxygenase before it is contacted with the auxiliary compound.

8. The method of claim 1 wherein the lignin sample is a plant biomass that further comprises cellulose or hemicellulose, and the auxiliary compound comprises a cellulase or a hemicellulase, and said cellulase or hemicellulase is provided in an amount sufficient to dissociate uncleaved lignin components or lignin macromolecules not degraded by the flavin-dependent monooxygenase from the at least partially degraded lignin.

* * * * *